(12) United States Patent
Milbocker et al.

(10) Patent No.: US 11,697,141 B2
(45) Date of Patent: *Jul. 11, 2023

(54) SELECTIVE TERMINATION OF SUPERHYDROPHOBIC SURFACES

(71) Applicant: BVW Holding AG, Cham (CH)

(72) Inventors: Michael Milbocker, Holliston, MA (US); Lukas Bluecher, Eurasburg (DE)

(73) Assignee: BVW Holding AG, Cham (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/669,091

(22) Filed: Feb. 10, 2022

(65) Prior Publication Data

US 2022/0161301 A1 May 26, 2022

Related U.S. Application Data (63) Continuation of application No. 15/898,500, filed on Jul. 16, 2018, now Pat. No. 11,278,941.

(Continued)

(51) Int. Cl.
| | |
|---|---|
| *B08B 17/06* | (2006.01) |
| *A61L 29/14* | (2006.01) |
| *A61L 31/14* | (2006.01) |
| *B29C 39/02* | (2006.01) |
| *B81C 1/00* | (2006.01) |

(Continued)

(52) U.S. Cl.
CPC .............. *B08B 17/06* (2013.01); *A61L 27/50* (2013.01); *A61L 29/14* (2013.01); *A61L 31/14* (2013.01); *B08B 17/065* (2013.01); *B29C 39/026* (2013.01); *B81C 1/00206* (2013.01); *C23C 16/04* (2013.01); *A61L 2400/12* (2013.01); *A61L 2400/18* (2013.01); *B29K 2067/046* (2013.01); *B29K 2075/00* (2013.01);

(Continued)

(58) Field of Classification Search
CPC .......... B08B 17/06; B29C 39/026; B32B 3/30
See application file for complete search history.

(56) References Cited

U.S. PATENT DOCUMENTS

| | | |
|---|---|---|
| 9,120,670 B2 | 9/2015 | Hulseman et al. |
| 9,908,274 B2 | 3/2018 | Hulseman et al. |

(Continued)

FOREIGN PATENT DOCUMENTS

| | | |
|---|---|---|
| WO | 2009070796 | 6/2009 |
| WO | 2011109793 | 9/2011 |

(Continued)

*Primary Examiner* — Zachary M Davis
(74) *Attorney, Agent, or Firm* — Patterson Intellectual Property Law, P.C.; Ryan D. Levy; Mark A. Kilgore (57) ABSTRACT

Provided herein is a hierarchical superhydrophobic surface comprising an array of first geometrical features disposed on a substrate comprising a first material and a terminal level disposed on the second features, wherein the terminal level comprises a second material, the second material being different from the first material. The second material has a hydrophilicity different from the hydrophilicity of at least one of 1) the hydrophilicity of the second material and 2) hydrophilicity induced by the hierarchical structure. The present disclosure further includes methods of preparing hierarchical superhydrophobic surfaces and medical devices comprising the hierarchical superhydrophobic surfaces.

20 Claims, 8 Drawing Sheets

Related U.S. Application Data (60) Provisional application No. 62/460,568, filed on Feb. 17, 2017.

(51) Int. Cl.
*C23C 16/04* (2006.01)
*A61L 27/50* (2006.01)
*B29K 67/00* (2006.01)
*B29K 75/00* (2006.01)
*B29K 83/00* (2006.01)
*B29L 31/00* (2006.01)

(52) U.S. Cl.
CPC ..... *B29K 2083/00* (2013.01); *B29L 2031/756* (2013.01); *B81B 2203/0361* (2013.01)

(56) References Cited

U.S. PATENT DOCUMENTS

| | | |
|---|---|---|
| 9,988,201 B2 | 6/2018 | Darin et al. |
| 10,377,044 B2 | 8/2019 | Hulseman et al. |
| 10,458,053 B2 | 10/2019 | Hulseman et al. |
| 10,575,667 B2 | 3/2020 | Hulseman et al. |
| 10,687,642 B2 | 6/2020 | Hulseman et al. |
| 10,889,005 B2 | 1/2021 | Hulseman et al. |
| 11,278,941 B2 * | 3/2022 | Milbocker .............. B08B 17/06 |
| 2013/0330501 A1 * | 12/2013 | Aizenberg .......... B81C 1/00349 428/116 |
| 2015/0368838 A1 | 12/2015 | Hulseman et al. |
| 2017/0014111 A1 | 1/2017 | Hulseman et al. |
| 2019/0062155 A1 | 2/2019 | Hulseman et al. |
| 2020/0338808 A1 | 10/2020 | Hulseman et al. |
| 2021/0086371 A1 | 3/2021 | Hulseman et al. |

FOREIGN PATENT DOCUMENTS

| | | |
|---|---|---|
| WO | 2012012441 | 1/2012 |
| WO | 2013003373 | 1/2013 |
| WO | 2013162482 | 10/2013 |

* cited by examiner

SELECTIVE TERMINATION OF SUPERHYDROPHOBIC SURFACES

CROSS-REFERENCE TO RELATED APPLICATIONS

This application is a continuation of U.S. application Ser. No. 15/898,500 filed Feb. 17, 2018, which claims the benefit of U.S. Provisional Application No. 62/460,568 filed on Feb. 18, 2017, the contents of which are hereby incorporated by reference in their entirety.

TECHNICAL FIELD

The present disclosure provides a hierarchical superhydrophobic surface, wherein a metastable Cassie-Wenzel wetting state forms when the surface is in contact with a wet surface. The present surfaces are resistant to structural degradation and reduction of tissue localization properties when used as a medical implant.

BACKGROUND

Tissue adherent implants are known that use a Cassie-Wenzel state to localize the implant. Such implants comprise a substrate onto which at least two geometric surface patterns are disposed. A hierarchical surface is a surface with geometrical features that can be grouped by size and those features are stacked.

A hydrophilic surface makes a contact angle with a drop of pure water that is less than 90 degrees. A superhydrophobic surface is a surface that has a contact angle with water of greater than 140 degrees. The notion of hydrophilicity has a kinetic interpretation as well. According to the Washburn model, hydrophilicity is related to the filling rate of capillaries. For example, a filling rate of about 2 mm/min for a glass capillary with an inner diameter of 5 nm corresponds to a contact angle of 80 degrees.

Hydrophilicity is also associated with surface energy. Generally, high surface energy corresponds to a hydrophilic surface, and low surface energy corresponds to a hydrophobic surface. Surface energy is a complex combination of the chemistry and the geometry of a surface.

There are four generally recognized wetting states: 1) Wenzel, 2) Cassie or Cassie-Baxter, 3) Wenzel-Cassie, and 4) hemi-wicking. A hierarchical surface may comprise any combination of these wetting states. Consider a surface comprising a substrate having a first level A and a terminal level B, and a drop of water that covers a region C of the substrate. Not all of the substrate in region C need be in contact with the water. A Wenzel state is a wetting state in which pure water contacts the entire surface of both levels A and B, and thus covers the entire surface of the substrate in the region C. A Cassie state is a wetting state in which the water is in contact with Level B only. Finally, a Wenzel-Cassie state is a wetting state in which the water is in contact with one level and only partially in contact with another level in the region C. A hemi-wicking state is any of the above three wetting states in which the water contacts a region outside of the region C.

A Wenzel wetting state is one which interacts with a wet surface initially by attracting water to the substrate, followed by water saturation and then vanishing of the attraction. A Cassie wetting state is one which interacts with a wet surface by repelling water from it. A Wenzel-Cassie wetting state both attracts and repels water on a wet surface, and consequently cannot be saturated without applying compression energy. Consequently, a hemi-wicking Wenzel-Cassie state would be particularly useful in surfaces that contacts living tissue.

All of these wetting states result from a complex interaction of the dipole nature of water with the dipole nature of the substrate and an interaction between the surface tension of water and the geometry of the substrate surface. In completely liquid environments, such as those found in the human body, water surface tension can result from water localized on hydrophilic regions of a substrate interacting with lipids localized on lipophilic regions of a substrate. Accordingly, while the four above identified wetting states traditionally are defined in a gas-water-solid system, analogous wetting states are obtained in a lipid-water-solid system. In most cases, hydrophobic regions on a hierarchical surface correspond to lipophilic regions when placed in a living body.

There is a need for superhydrophobic hierarchical contact surfaces that are useful particularly for medical implants and other contact indications. Such surfaces would provide appropriate issue adherence. Furthermore, there is a need for superhydrophobic hierarchical surface having improved mechanical features such that they do not contain geometrical features that are subject to distortion or fouling. The present disclosure addresses these needs.

BRIEF SUMMARY

The present disclosure generally relates to a hierarchical superhydrophobic surface comprising an array of first geometrical features disposed on a substrate comprising a first material, and an array of second geometrical features disposed on the first features to form a hierarchical structure and a terminal level disposed on the second features, wherein the terminal level comprises a second material, the second material being different from the first material.

It has been surprisingly discovered that a hierarchical superhydrophobic surface in which the terminal level has been replaced by a smooth hydrophilic substance displays a Wenzel-Cassie behavior, in contradiction with classical wetting models. Indeed, substitution of geometrically induced hydrophilicity with chemical hydrophilicity, and substitution of a geometrically induced hydrophobicity with chemical hydrophobicity, can be applied at any level of the hierarchical surface. For example, a smooth hydrophobic hierarchical substrate coated in regions with a smooth hydrophilic substance can act as pinning sites for Wenzel-Cassie states.

Generally, the present hierarchical surfaces provide novel wetting states that result from localized variation in surface energy resulting from combinations of chemical surface energy and geometrical surface energy. In addition to providing novel wetting states, in consideration of the unexpected observation above, terminal level geometrical features, which may be susceptible to mechanical distortion or fouling may be beneficially replaced with a terminal smooth substance. For example, a terminal pattern level formed by the geometrical features may be replaced. While not being bound by theory, it is understood that it is the differences in surface energy in regions and their relative sizes that creates the wetting states of the present disclosure. Accordingly, in some cases a hydrophobic level A terminated with a hydrophilic substance behaves similarly to a hydrophilic level A terminated with a hydrophobic substance.

In one or more embodiments, at least one of the first geometrical features, second geometrical features or terminal level is modified to enhance fixity between the hierarchical structure and a living tissue. In one or more embodiments, a functional coating is disposed on at least a portion of the hierarchical structure.

In one or more embodiments, the hierarchical structure is characterized by a specific surface area of at least about 100 times the specific surface area of a flat solid substrate of the same dimensions.

In one or more embodiments, the solid substrate of the hierarchical structure is compact or porous.

In one or more embodiments, the substrate is inorganic or organic. In one or more embodiments, the substrate comprises polylactic acid, polyurethane, polypropylene, silicone, or combinations thereof.

In one or more embodiments, the geometrical surfaces comprise pillars, two-dimensional sinusoids, triangular prisms, flutes or combinations thereof. In one or more embodiments, the pillars are cylindrical structures with diameters ranging from about 1 to about 10 microns at one level and from 10 to 30 microns at another level, and aspect ratios ranging from about 1 to about 10.

In one or more embodiments, the terminal level comprises a hydrophilic solid. In one or more embodiments, the terminal level comprises a hydrophobic solid.

In one or more embodiments, the hierarchical surface is disposed on or formed as a part of a medical device or implant. The surface advantageously affixes the device or implant to tissue in vivo.

In one or more embodiments the terminal level is functionalized by a method selected from the group (a) solution chemistry, (b) chemical vapor deposition, (c) plasma deposition, (d) atomic layer deposition, (e) physical vapor deposition, or a combination thereof.

A superhydrophobic hierarchical surface can be subjected to solution-based chemistry near the geometric feature with a fluid. In certain embodiments, the coating chemistry includes precipitation reactions, but, other processes are also possible, such as molecular adsorption, colloidal deposition, polymerization, and catalytic reactions.

In one embodiment, solid precipitates are grown from solution by heterogeneous nucleation onto the exposed geometric features of the surface.

In one aspect, a method of localized formation of a material includes contacting a superhydrophobic hierarchical surface comprising geometrical features with a non-wetting fluid comprising a material to be locally formed on features or a precursor thereto, where the superhydrophobic surface and the fluid are selected such that the fluid wets only an upper portion of the geometrical features; and causing the material to form on the features. In one or more embodiments, the terminal level comprises micro-scale or nano-scale pillars, or the terminal level can comprise a random array of isolated or interconnected geometrical features.

In one or more embodiments, the terminal level is chemically treated to include either a hydrophobic coating or a hydrophilic coating.

In one or more embodiments, the terminal level is treated to provide bonding or adherent interaction of the coating material and the terminal surface. For example, the terminal level may selectively be treated with ionizing radiation.

In one or more embodiments, the coating material comprises molecules, polymers, colloidal particles, or mixtures thereof. In some embodiments, the material is catalytic, magnetic, optically-active, piezoelectric or bioactive.

In another aspect, a method of localized formation of a coating material includes providing a superhydrophobic hierarchical surface comprising hierarchical geometric features said features comprising at least two regions having different surface properties, contacting the surface with a fluid, said liquid comprising a material to be locally formed on the geometrical features, or a precursor thereof, wherein the surface properties of the two or more geometrical features and the fluid are selected such that the fluid wets one or the other or both of the at least two regions, and causing the material to selectively deposit at one or the other or both of the at least two regions.

In one or more embodiments, the method further includes contacting the coated geometrical features with a second fluid, said second fluid comprising a second material to be locally deposited, or a precursor thereof, wherein the material is deposited over both the first and second regions.

In one or more embodiments, the superhydrophobic hierarchical surface comprises pillars, two-dimensional sinusoids, and flutes, or the surface comprises an array of silicon or polymeric pillars, or the surface comprises a random array of geometric features. In one or more embodiments, the geometric features are chemically treated to provide a hydrophobic layer, a hydrophilic layer, or a tissue bonding or tissue adherent layer.

In one or more embodiments, the adherent material is catalytic, magnetic, piezoelectric or bioactive. In other embodiments, the adherent material comprises organic or inorganic precipitates, molecules, polymers, colloidal particles, or mixtures thereof.

In one or more embodiments, the tissue bonding material is adherent to an uppermost portion of the terminal level.

In one or more embodiments, the geometrical features comprise at least two regions having different surface properties, and the adherent material is adherent to at least one of said two regions.

The present disclosure further provides methods of producing the aforementioned hierarchical superhydrophobic surfaces comprising: providing an array of a first geometrical feature disposed on a substrate, and a second geometrical feature disposed on the first feature to form a hierarchical structure, and forming the terminal level by a method selected from solution chemistry, chemical vapor deposition, plasma deposition, atomic layer deposition, physical vapor deposition, or a combination thereof.

The present disclosure further provides a medical device comprising the aforementioned hierarchical superhydrophobic surfaces.

DETAILED DESCRIPTION

The following description is an exemplification of the principles of the present disclosure and is not intended to limit the disclosure to the particular embodiments illustrated herein.

The present disclosure provides, in some embodiments, a hierarchical superhydrophobic surface comprising an array of first geometrical features disposed on a substrate comprising a first material, and an array of second geometrical features disposed on the first features to form a hierarchical structure and a terminal level disposed on the second features, wherein the terminal level comprises a second material, the second material being different from the first material.

In particular embodiments, the second material has a hydrophilicity that differs from the hydrophilicity of the first material. In other embodiments, the second material has a hydrophilicity that differs from the hydrophilicity induced by the hierarchical structure of the surface.

The geometric features of the present disclosure may have any shape. For example, the features may be pillars (such as cylindrical pillars), sinusoids, triangular prisms, flutes, ridges, squares, rectangles, ovals and the like. In a particular embodiment, the geometrical features are pillars. In other embodiments, the features are a combination of pillars and sinusoids. In a particular embodiment, the substrate comprises a sinusoidal shape, and the first and second geometric features comprise pillars. The terminal level may further comprise pillars having a different material from the substrate and first and second pillars. In a further embodiment, the second set of pillars further comprises flutes or ridges disposed along a vertical axis of the pillar.

In certain embodiments, at least one of the geometric features can be coated with a hydrophobic or hydrophilic material.

In some embodiments, the terminal level comprises a smooth functional coating, such as a smooth tissue attractive coating.

In certain embodiments, the second material disposed on the terminal level is bonded or adherent to the terminal level via van der Waals interaction, covalent interaction, ionic interaction, hydrogen bonding, or combinations thereof.

In certain embodiments, the terminal level comprises a smooth functional coating. The functional coating may be a tissue attractive coating.

In some embodiments, the first geometrical features comprise a width or diameter ranging from about 1 micron to about 100 microns, preferably about 10 microns to about 50 microns, and the second geometrical features have a width ranging from about 100 nm to about 10 microns, preferably about 1 micron to about 10 microns.

In some embodiments, the first and second geometrical features have an aspect ratio ranging from about 1 to about 10.

In some embodiments, the first geometrical features have a pitch ranging from about 10 to about 1000 microns, about 10 to about 500 microns, about 50 to about 100 microns or about 100 to about 1000 microns. The second geometric features may have a pitch ranging from about 10 nm to about 100 microns, about 1 micron to about 100 microns, about 1 micron to about 50 microns or about 10 micron to about 50 microns.

In some embodiments, the first material comprises polylactic acid, polyurethane, polypropylene, silicone or a combination thereof. In certain embodiments, the second material comprises polylactic acid, polyurethane, polypropylene, silicone or a combination thereof, provided that the second material is different from the first material.

A superhydrophobic surface is a surface with at least a portion of its surface making a contact angle with water greater than 140 degrees. A hierarchical surface is a surface with geometrical features that can be grouped by size and those features are stacked. For example, a surface may have one set of features characteristically of sizes between 100 nm and 1 micron, and another set of features characteristically of sizes between 5 microns and 10 microns, wherein substantially all of the features on a surface can be placed in either group, with very few features in the size ranges of 1 micron to 5 microns, <100 nm, and >10 microns. Each of the characteristic size ranges are called levels. The level corresponding to the smallest characteristic size is called the terminal level.

A surface comprised of levels A and B where the size of A is greater than the size of B, then the surface is said to be arranged hierarchically if the features of B are on top of the features of A. Examples may include 1) small pillars arranged on the flat top of larger pillars, 2) flutes or ridges on the sides of pillars, and 3) pillars arranged on a surface resembling a two-dimensional sinusoid.

Hydrophilicity can result from the chemical structure of a material, or the surface geometry of a material. When the surface geometry changes the hydrophilicity of the substrate, then the changed hydrophilicity is called an induced hydrophilicity. Chemically hydrophilic materials can be made more hydrophobic with the addition of surface texture, and chemically hydrophobic materials can be made more hydrophilic with the addition of a surface texture. A material that comprises most of the surface area of a hierarchical surface is called a substrate.

A superhydrophobic surface is metastable if portions of the surface wet or attract water and other portions of the surface resist wetting or repel water. Hierarchical surface patterns are generally responsible for metastability, where the hydrophilicity at each level is different. Generally, there is at least one level that is hydrophilic and at least one other level that is hydrophobic.

The notion of hydrophilicity has a kinetic interpretation as well. According to the Washburn model, hydrophilicity is related to the filling rate of capillaries. For example, a filling rate of about 2 mm/min for a glass capillary with an inner diameter of 5 nm corresponds to a contact angle of 80 degrees.

Hydrophilicity is also associated with surface energy. Generally, high surface energy corresponds to a hydrophilic surface, and low surface energy corresponds to hydrophobicity. Surface energy is a complex combination of the chemistry and the geometry of a surface.

There are four generally recognized wetting states: 1) Wenzel, 2) Cassie or Cassie-Baxter, 3) Wenzel-Cassie, and 4) hemi-wicking. A hierarchical surface may comprise any combination of these wetting states. Consider a surface comprising a substrate having a first level A and a terminal level B, and a drop of water that covers a region C of the substrate. Not all of the substrate in region C need be in contact with the water. A Wenzel state is a wetting state in which pure water contacts the entire surface of both levels A and B, and thus covers the entire surface of the substrate in the region C. A Cassie state is a wetting state in which the water is in contact with Level B only. Finally, a Wenzel-Cassie state is a wetting state in which the water is in contact with one level and only partially in contact with another level in the region C. A hemi-wicking state is any of the above three wetting states in which the water contacts a region outside of the region C.

A Wenzel wetting state is one which interacts with a wet surface initially by attracting water to the substrate, followed by water saturation and then vanishing of the attraction. A Cassie wetting state is one which interacts with a wet surface by repelling water from it. A Wenzel-Cassie wetting state both attracts and repels water on a wet surface, and consequently cannot be saturated without applying compression energy. Consequently, a hemi-wicking Wenzel-Cassie state is particularly useful in surfaces that contacts living tissue. A hemi-wicking Wenzel-Cassie state resists saturation (maintains grip) even in the presence of water-eluting living tissue. For example, the surfaces of the present disclosure are usefully hemi-wicking and can maintain adherence to a melting ice cube, even at angles as great at 90 degrees to the horizon. Accordingly, the surfaces of the present disclosure typically comprise 3 or more levels, wherein the first level is hemi-wicking, the second level is hydrophilic or hydrophobic, and the third level is more hydrophilic or hydrophobic than the second layer.

All of these wetting states result from a complex interaction of the dipole nature of water with the dipole nature of the substrate and an interaction between the surface tension of water and the geometry of the substrate surface. In completely liquid environments, such as those found in the human body, water surface tension can result from water localized on hydrophilic regions of a substrate interacting with lipids localized on lipophilic regions of a substrate. Accordingly, while the four above identified wetting states traditionally are defined in a gas-water-solid system, analogous wetting states are obtained in a lipid-water-solid system. In most cases, hydrophobic regions on a hierarchical surface correspond to lipophilic regions when placed in a living body. A Wenzel-Cassie state between a hierarchical superhydrophobic surface and living tissue is referred to as tissue bonding hydrophobicity.

One of the functional components used in the present surfaces may be hydrophobic, and may contain a fluorine-containing moiety which associates with gas phase oxygen or alternatively associates with lipophilic substances. The second functional component may be hydrophilic, and when implanted readily associates with water. Upon implantation, the two functional components set up domains of hydrophobic constituents derived from the implant environment and domains of hydrophilic constituents derived from the implant environment. The structure is selected such that the implant derived hydrophobic constituents bead or possess high surface tension juxtaposing the regions of implant derived hydrophilic constituents. The degree to which the implant derived constituents fill the geometry of the surface determines whether a Cassie or wettable Cassie state exists locally. Depending on the time and conditions surrounding the implant, either the aqueous or lipo fractions may be, relatively, more spreading. Therefore, the implant surface may be simultaneously adhesive to hydrophobic substances and repulsive to hydrophilic substances, or vice versa, and this condition may be designed to change with time.

The following definitions apply to the present disclosure. A hydrophilic surface is a surface that makes a contact angle with a drop of pure water that is less than 90 degrees. A surface A is said to be more hydrophilic than another surface B if the contact angle for A is less than the contact angle for B. Hydrophobicity is the inverse of hydrophilicity. When the water drop is substituted with an oil drop, then the corresponding terms are lipophilic and lipophobic.

Figure 1A:
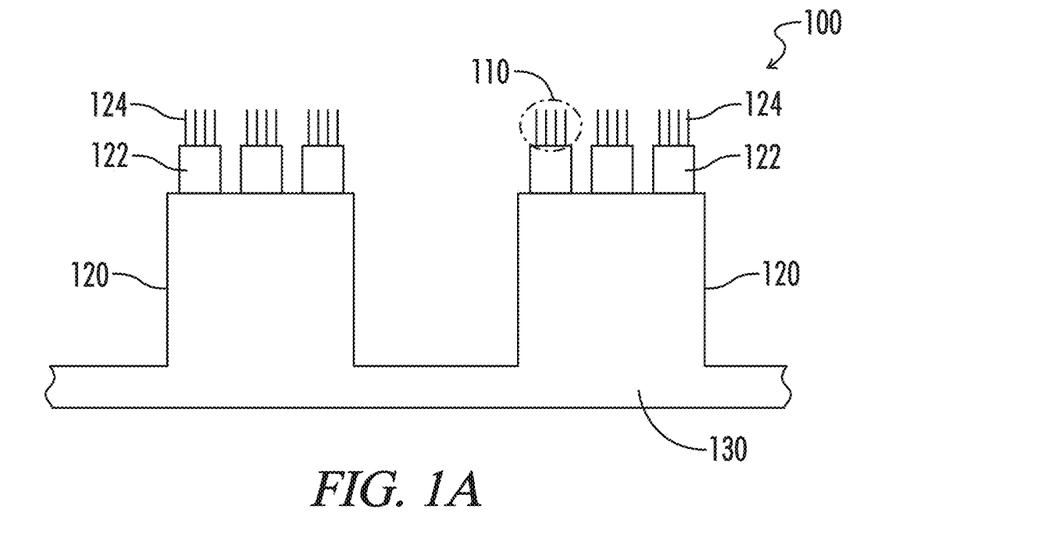
FIG. 1A depicts a hierarchical superhydrophobic surface comprises arrays of hierarchically disposed geometric surface features.

Referring to FIG. 1A, a hierarchical superhydrophobic surface 100 can be contacted with a fluid 110 containing a material to be locally deposited at the terminal level of the surface to obtain low contact angles. In certain embodiments, the surface without the local deposition of material forms water contact angles greater than or equal to 140 degrees. Hierarchical superhydrophobic surfaces have geometric features that are typically on the order of microns or nanometers in at least one dimension. The surface structures can be an ordered or disordered array of protrusions stacked hierarchically.

Any superhydrophobic surface may be used, including electrospun polymer arrays, ordered arrays of pillars, a suitably randomly rough surface, a layer of spheres, lines, and the like which are chemically hydrophobic or are geometrically hydrophobic.

In some embodiments, the superhydrophobic surface can include nano and micro surface structures that result in a high degree of surface roughness that is hemi-wicking, such as relatively large amplitude (100 to 1000 microns) two-dimensional sinusoids. High amplitude surface roughness can substantially increase the tissue fixing propensity of the hierarchical superhydrophobic surfaces by preventing fluid saturation of the surface, and thereby cause the phenomenon of tissue bonding superhydrophobicity.

The spacing, height, and other dimensions of the features on the geometric features may be matters of discretion. For example, the dimensions of the structures may be on the order of angstroms, nanometers, or microns.

These structures can be fabricated from any biocompatible polymer, preferably with relatively low flexural modulus, for example, silicone, polyurethane, polypropylene, polylactic acid, or an organic polymer. Exemplary superhydrophobic surfaces can include arrays of organic micro-pillars, such as polylactic acid micro-pillars that are obtained from a negative mold formed by etching the surface of a silicon wafer. Other biocompatible hydrophobic materials for use in the present surfaces include fluorinated polymers, e.g., PTFE and hydrophobic silanes.

The present surfaces are advantageously treated to enhance tissue bonding hydrophobic properties of the surface. For example, a low surface energy material can be deposited on the geometrical features to increase the in vivo Cassie-Wenzel nature of the features. Conversely, a high surface energy material can be deposited on geometrical features to increase the in vivo Cassie-Wenzel nature of the features.

In certain embodiments, the shape of the micro-pillars can provide greater flexibility in obtaining the desired tissue bonding superhydrophobic surfaces. As one particular non-limiting illustrative example of a hierarchical superhydrophobic surfaces, hydrophobic pillars with a flared end on top of which is deposited a hydrophilic medium uniquely sustains a Cassie-Wenzel state in vivo by preventing saturation wetting even for liquids that have a relatively low surface contact angle, such as angles between 40° and 90°.

Terminal Level Functionalization

The hierarchical superhydrophobic surfaces of the present disclosure include those that can be terminally functionalized by any suitable and/or desirable means. For example, the desired regions near the tips of the superhydrophobic surface can be functionalized with any desired groups, such as groups that are capable of electrostatic, covalent, hydrogen bonding, and/or van der Waals interactions.

In one embodiment, surface structures having a terminal fine structure can be functionalized by adhesion with surface groups that replace the fine structure with a smooth surface with a specific chemical hydrophilicity, thus replacing geometric hydrophilicity with chemical hydrophilicity.

In certain embodiments, the geometric features of the hierarchical superhydrophobic surfaces can be functionalized in a variety of ways to provide a surface for precipitation, adsorption or deposition of material from solution to occur. In one embodiment, a geometric feature can be treated to deposit a layer of gold, which can then be reacted with a variety of materials, e.g., hydrophobic thiol compound, to form a hydrophobic surface. Exemplary thiolated molecules include poly(styrene-co-2,3,4,5,6-pentafluorostyrene-SH), poly(methyl methacrylate-co-pentafluorooctyl methacrylate-SH), but in general any fluorinated or methylated thiol can be utilized. The tips of the geometric feature can be further selectively functionalized by contacting the thiol-treated surface with a solution that contains another compound having the desired surface properties. Some exemplary molecules include carboxylic acid-terminated thiols, sulfonated thiol molecules, hydroxyl-terminated thiols, PEG-terminated thiols, and the like.

While not being bound by theory, it is believed that geometrically hydrophilic terminal structures can be locally replaced by chemically hydrophilic smooth surfaces. Doing so makes the present surfaces more mechanically robust by elimination of small scale features that may not reproduce well or degrade with use.

In another embodiment, a hydrophobic layer can be deposited on the surface of the geometric features. For example, if the surface substrate is made of silicone, then the surface can be functionalized with a fluorinated silane. The tips of the geometric features can be further selectively functionalized by contacting the hydrophobic surface with a solution that contains a tissue attractive component (e.g., oxides of dextran). By controlling the superhydrophobic character of the surface and/or the fluid, the fluid can wet only desired regions of the tips and selectively functionalize the exposed tips of the surface. Exemplary molecules include carboxylic acid terminated silanes, sulfonated silanes, hydroxyl-terminated silanes, PEG-terminated silanes.

The geometric features can be also functionalized using a microcontact approach, by gently applying a roller to the tips of the nanostructured surface. In another approach, the hierarchical surfaces can be placed top-side down on a surface coated with a functionalizing moiety, and the functionalizing moiety deposited on the terminal level by a variety of means. For example, the deposition means may include polymerization, evaporative casting, UV-curing, or any method generally known to chemistry that induces a phase transition from a liquid state to a solid state.

In some embodiments, the superhydrophobic surface can be selectively functionalized at any region along a dimension, e.g., the length, of the geometric feature. For example, by controlling the interaction of the fluid to the superhydrophobic surface, a first fluid that contacts the terminal level of the superhydrophobic surface can be introduced. The first fluid can contain desired materials which can adhere to the terminal level of the superhydrophobic surface and provide desired first functional groups. A second fluid which penetrates to a deeper level than the first fluid into the superhydrophobic surface can be introduced to the superhydrophobic surface. The second fluid can contain desired materials which can adhere below the terminal level or deeper on the level adjacent to the terminal level and provide desired second functional groups. A third fluid which penetrates even deeper than the second fluid into the superhydrophobic surface can be introduced to the superhydrophobic surface. The third fluid can contain desired materials which can adhere below the second functional group and provide desired third functional groups. Alternatively, the three fluids can selectively adhere to discrete levels.

In some embodiments, the terminal level comprises three different structures all of approximately the same spatial dimension. Accordingly, the superhydrophobic surface has three different functionalities near the tip of the superhydrophobic surface. The structures may differ by their pitch, geometric form, or aspect ratio. This approach can be implemented as desired to provide any number of desired functional groups near the tip of the superhydrophobic surface. As an alternative embodiment to achieve the linear sequence of deposition of different materials, an array of nanowires can be first covered completely with a layer of sacrificial material (e.g., polymer). Then the polymer layer can be etched away to reveal the tips of the posts that are then functionalized as described above (either using the layer of gold which is then functionalized with a thiol or, in case of Si structures, using the appropriate silane solution). The polymer layer can then be partially etched further to reveal the next band on the wire, which is functionalized as described above. The process can be repeated to produce the desired number of functionalized bands. At the end, the remaining layer of the sacrificial material can be etched and the bottom of the nanowires can be rendered hydrophobic. Suitable polymers may be chosen from those known in the art that are susceptible to etching, such as, photoresist or polystyrene.

Terminal Level Substitution

In another embodiment, the geometric features can be functionalized using stepwise fabrication techniques. By way of example, the spaces between features can be filled with a sacrificial material, which can then be selectively removed to expose the distal ends of the structure. The exposed ends can be functionalized, for example, using any of the methods and solutions described above, and the remaining sacrificial material can be removed. The remainder of the superhydrophobic surface can be treated to apply a hydrophobic coating.

A hierarchical mould-based dewetting process may be used to isolate the terminal level from the other levels of the surface. The first step comprises placing a UV-curable hydrophobic polymer resin, for example perfluoropolyether, confined to be between a lower MHSS and a flat upper sheet made of a hydrophilic polymer resin, for example, polyurethane acrylate. The second step comprises UV-curing the hydrophobic polymer resin and subsequently pulling back the flat upper sheet, exposing the terminal level of the MHSS without residual layer of hydrophobic polymer resin. A unique feature of this method is the capability of excluding a residual layer at the terminal level by exploiting a high wettability difference between and taking advantage of the hierarchical structure of the hierarchical superhydrophobic surface. The third step comprises applying the terminal substance, replacing the hydrophilic sheet, applying pressure, and allowing the applied substance to cure by solvent diffusion or some other method known in the art. In this instance, no residual layer of terminal substance remains anywhere outside the locus of the terminal level. The fourth step comprises peeling back the hydrophilic cover sheet, and then peeling away the UV-cured hydrophobic layer, leaving a hierarchical superhydrophobic surface with a terminal layer coated with a terminal substance. When the UV-curable resin is dropwise placed on the surface and covered by the hydrophilic sheet, the resin spontaneously spreads inside the confined spaces and a majority of the resin is squeezed out of the assembly on an application of pressure and due to the large affinity difference (dewetting) between the surface and UV-curable resin.

Precipitate Nucleation

Useful embodiments of terminal level deposition by precipitation are provided. In some embodiments, the precipitate or deposited growths are designed to remain adherent to the tips of the surface structure. In some embodiments, the method is used to provide adherent deposition and growth of material on the terminal level. The method can be used to incorporate useful materials onto a terminal level micro-pillar array, such as crystalline materials, especially materials with a large electric dipole or magnetic dipole moment. Still other materials include spin gel materials with anti-reactive oxygen species properties that could alter or inhibit the formation of ingrowth tissue, e.g., tissue adhesions.

Figure 1B:
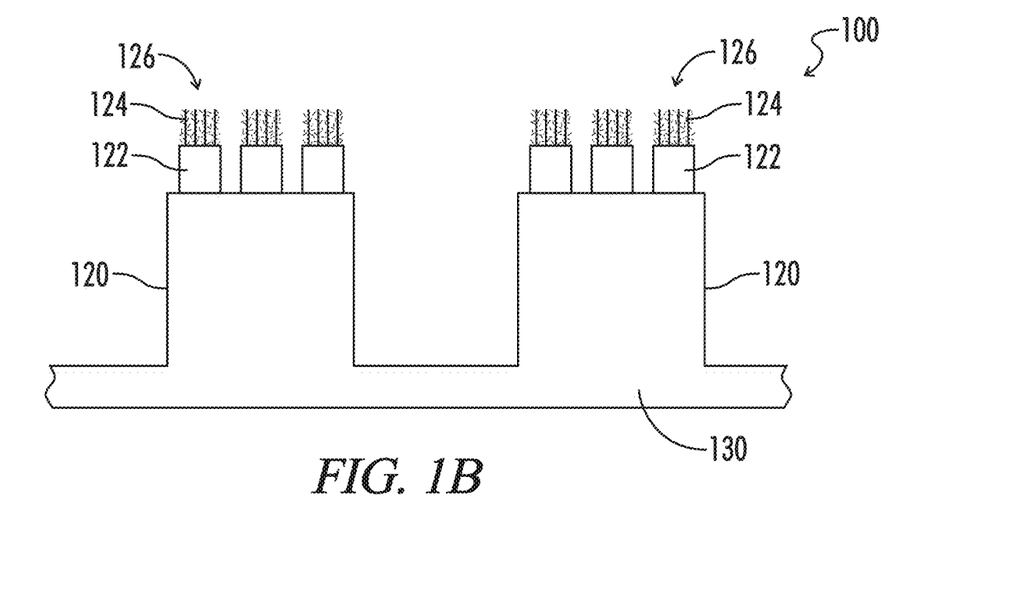
FIG. 1B depicts the surface of FIG. 1A, in which a second material has been deposited on the terminal features.

Referring to FIG. 1A, which depicts a side view of a superhydrophobic surface 100, an array of micro pillars 120 are disposed vertically on substrate 130. Substrate 130 can, in some embodiments be a medical device or implant, such as an anti-adhesive sheet. A second level array of micropillars 122 are disposed vertically on the first pillars 120. A third set of structures, which may be micro or nanopillars or wires 124 is disposed on the second level pillars 122. A fluid 110 to be deposited on the terminal level can be a supersaturated solution with a soluble form of the material to be deposited or a precursor thereof, or a suspension of colloidal particles. As shown in FIG. 1B, deposition from fluid 110 provides a terminal level 126 having a different chemical composition from the substrate material. Terminal level 126 can be a rough disordered surface, while in other embodiment 126 may be a smooth surface. Nucleation deposition methods known in the art include deposition through a temperature- or evaporation-induced solubility change, an insoluble reaction product, the addition of a common ion, or introduction of an immiscible solvent, polymerization, addition of reactive agents to liquid, exposing liquid to gas or vapor reagents that induce precipitation, reaction to an insoluble product, and the like.

The solution 110, e.g., an aqueous solution, can be in contact in limited regions of the surface, where the superhydrophobicity of the terminal level can interact with the fluid in a manner to minimize surface contact. Accordingly, the terminal pillars 124 provide sites for nucleation deposition of desired material. The point contacts of the surface with the fluid can act as nucleation sites and/or sites for other chemical processes that are involved in the deposition process. For example, if the conditions are suitable for heterogeneous nucleation, then precipitation can occur in a controlled, localized manner only on those exposed tips. The superhydrophobic terminal level could further be chemically functionalized, to influence the precipitate growth. For example, the superhydrophobic surface can be treated to increase its hydrophobicity, to increase adherent interactions, e.g., covalent or ionic interactions, with the deposited material and/or to direct deposition to occur at selected locations and/or in a selected order. In some embodiments, if the non-wetting solution is removed by wicking or evaporation, the desired localized precipitates can remain on the terminal levels.

Figure 2:
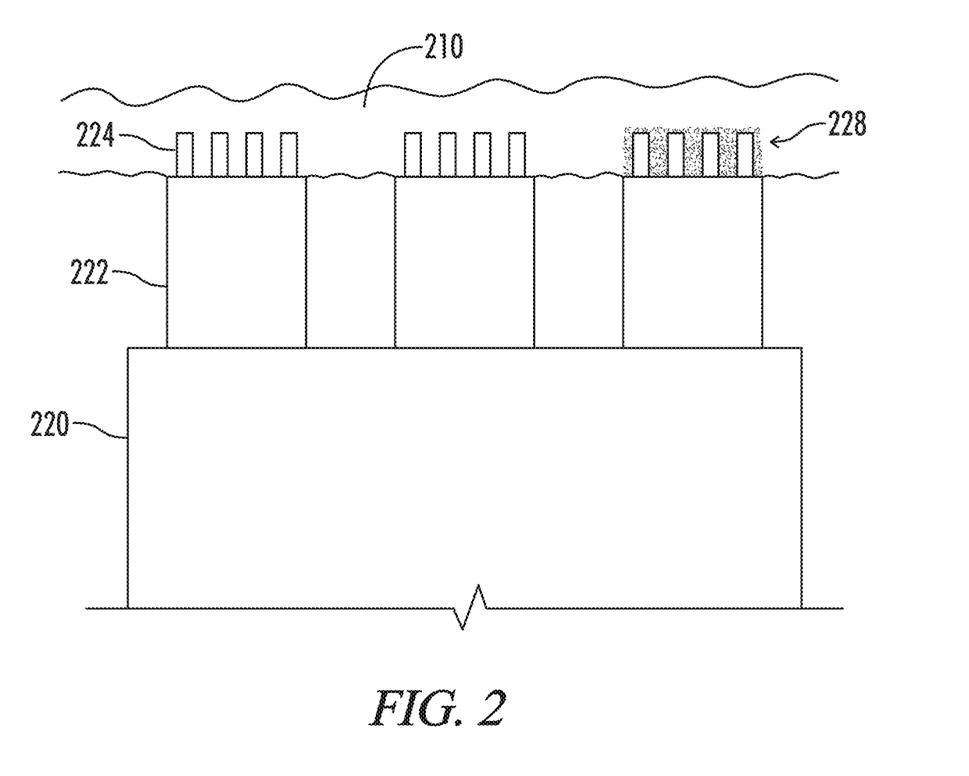
FIG. 2 depicts a schematic of nucleation precipitation on the tips of a hierarchical surface.

FIG. 2 provides a schematic illustration of a method for nucleation precipitation on the tips of geometric features such as pillars, pyramids, fibers and the like. In FIG. 2, geometric feature 220 comprises a second features 222 disposed thereon, such that 222 is the terminal level of the superhydrophobic surface. A third feature 224 is disposed on feature 222. These features may be, in some embodiments, pillars. Nucleation 228 can begin from a supersaturated solution 210 that contacts the exposed terminal level. Over time, the adherent growth of precipitates 228 can increase the size of the deposited material on and between the micro-pillars 224. The localized precipitate deposits remain on the micro-pillars 224 of the terminal level, both during growth and following removal of the functional solution.

One exemplary way that such adherent deposition can be achieved is by the chemical functionalization of the tips of the terminal level structures with functional groups that provide strong association with the deposited material. Functional groups can improve adherence by a variety of physical phenomena, including electrostatic, van der Waals, hydrogen bonding, and/or covalent forces. The functionalized micro-pillars with adherent deposited material can interact with living tissue to reduce Cassie-Wenzel saturation and increase the strength and duration of superhydrophobic tissue bonding.

Many different applications utilizing the structure formed in FIG. 2 can be envisioned. For example, localized nucleation and growth of an adherent particle can be used to deposit a material 228 that is, for example, hydrophilic, hydrophobic or tissue adherent, on a micro-pillar terminal level 224. In the case of a hydrophilic termination, when a surface is placed in contact with tissue, the functionalized micro-pillars 228 of the terminal level create pinning centers in a Wenzel wetting state and the first level 220 creates a Cassie wetting state. As a result, the tissue is fixed in shear relative to the hierarchical superhydrophobic surface.

As another non-limiting example of different applications that can be envisioned, adherent deposition of materials can occur at different locations on the levels of the surface in coordination with the location and nature of the chemical functionality on the structure and the position of the tissue interface. Chemical functionality can be used to control the propagation and selection of cells across the tissue interface. The selective surface functionalization of the levels of the hierarchical superhydrophobic surface makes it possible to control the speed and type of cells that are adherent and can propagate across the surface.

For example, a hierarchical superhydrophobic surface formed from a biocompatible polymer such as polyurethane can be functionalized with one or more functional groups. As noted above, functional groups can change the surface properties of the terminal level of the hierarchical superhydrophobic surface relative to the rest of the surface, and can, for example, improve the cell adherent properties of the functionalized region. In some embodiments, the various levels can be selectively surface functionalized using two or more functional groups. For example, a hierarchical structure of a first level of pillars with a terminal level of pillars on the ends of the first level pillars can be coated at the terminal level that completely encapsulates the terminal level pillars and a second functional coating selectively coats the sides of the first level pillars.

Figure 3:
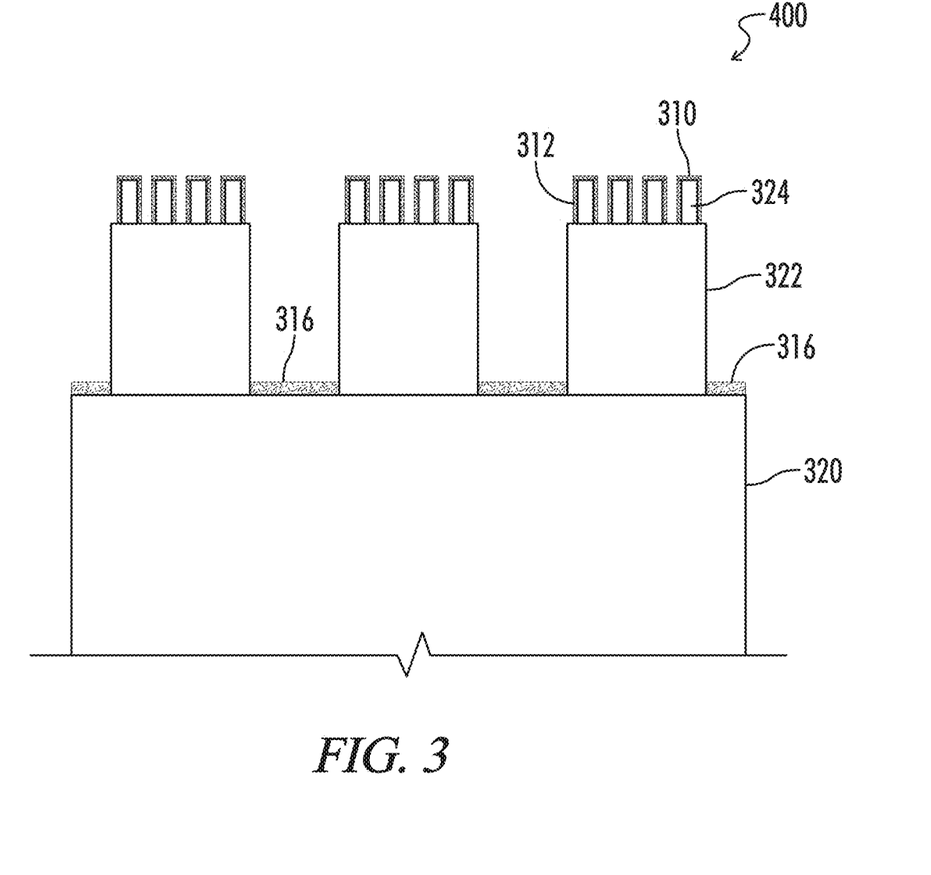
FIG. 3 depicts a hierarchical superhydrophobic surface of the present disclosure in which several functional layers are provided at the terminal level and on other geometrical features on the surface.

FIG. 3 is a side view of a hierarchical superhydrophobic surface 300 comprising geometrical features having multiple levels functionalized. The geometrical features in some embodiments are pillars. The surface comprises a base level 320 having a second geometric feature 322 disposed thereon. A third feature 324 is disposed on the second feature providing the terminal level. The top area of terminal level 324 comprises a functionalized layer 310 comprising a first functional group F1, a second functionalization layer 312 comprising a second functional group F2 coats the walls of third level features 324 having functional group F2, and a third functionalization layer 316 having functional group F3 coating the hemi-wetting two-dimensional base level 320. As a result of this functionalization, selective cellular growth can be achieved at the various levels of hierarchical superhydrophobic surface.

To achieve the multiple level deposition of materials as shown in FIG. 3, a solution can be provided that contains several components, each of which selectively deposits on individual specific levels. Alternatively, the materials can be deposited by expositing the surface to a series of solutions, each of which is selected to deposit a specific compound at a specific location. The subsequently deposited materials do not deposit on top of the previously deposited material(s).

Surface Treated Electrowritten Superhydrophobic Adherent Fibers

Figure 4:
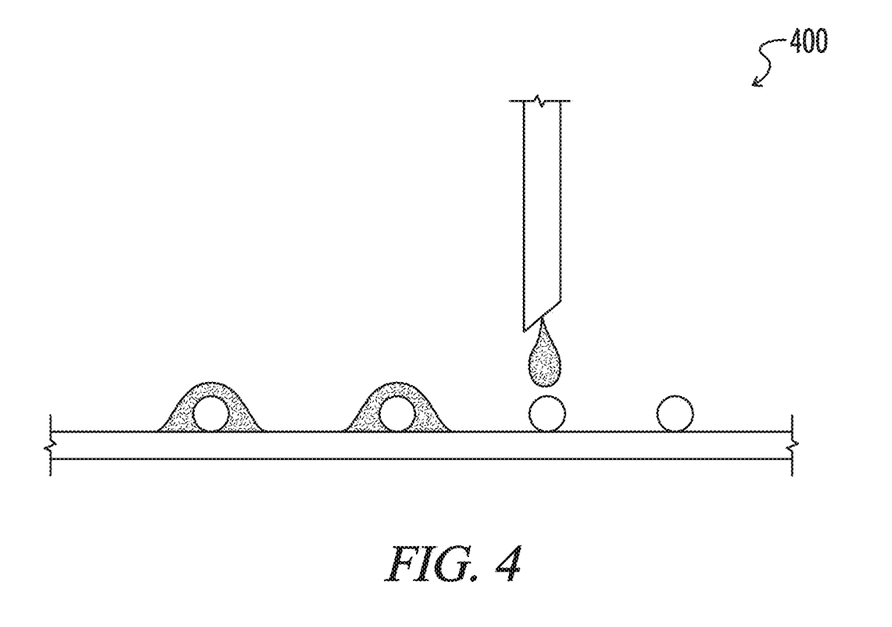
FIG. 4 is a schematic illustrating a precipitate writing process useful for functionalizing geometric surface features of the present disclosure.
Figure 5A:
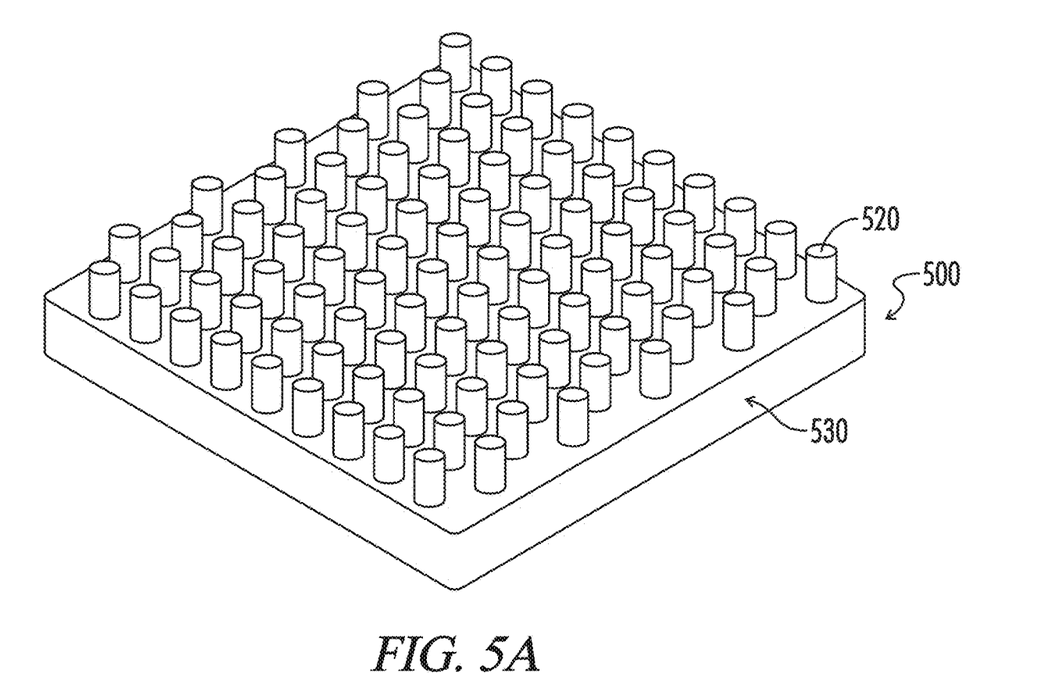
FIG. 5A depicts a perspective view of a hierarchical superhydrophobic surface according to the present disclosure.
Figure 5B:
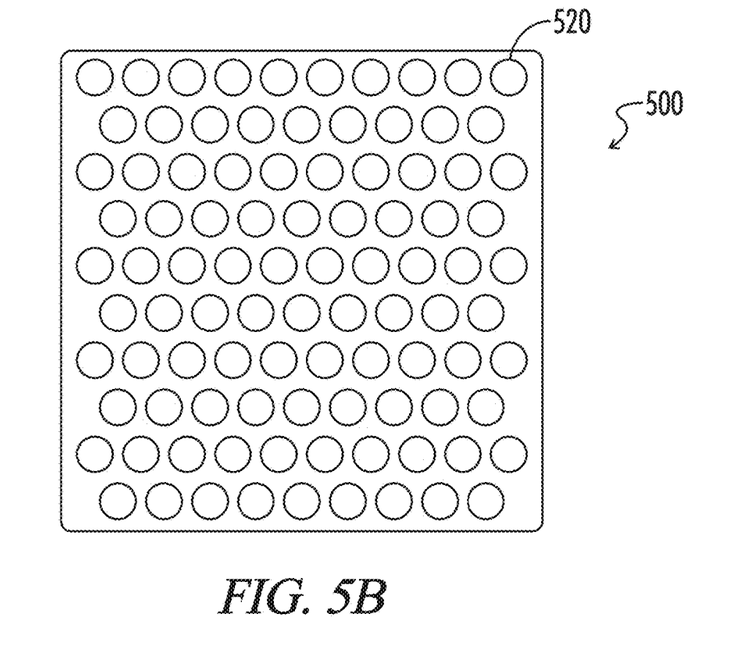
FIG. 5B is a top view of the array.
Figure 5C:
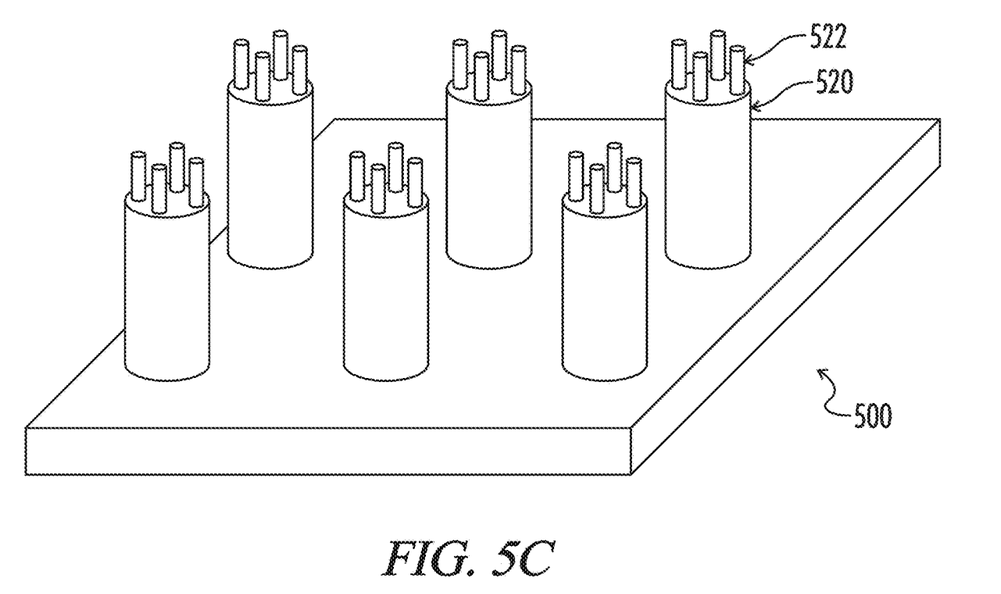
FIG. 5C is an expanded perspective view of the hierarchical superhydrophobic surface.
Figure 5D:
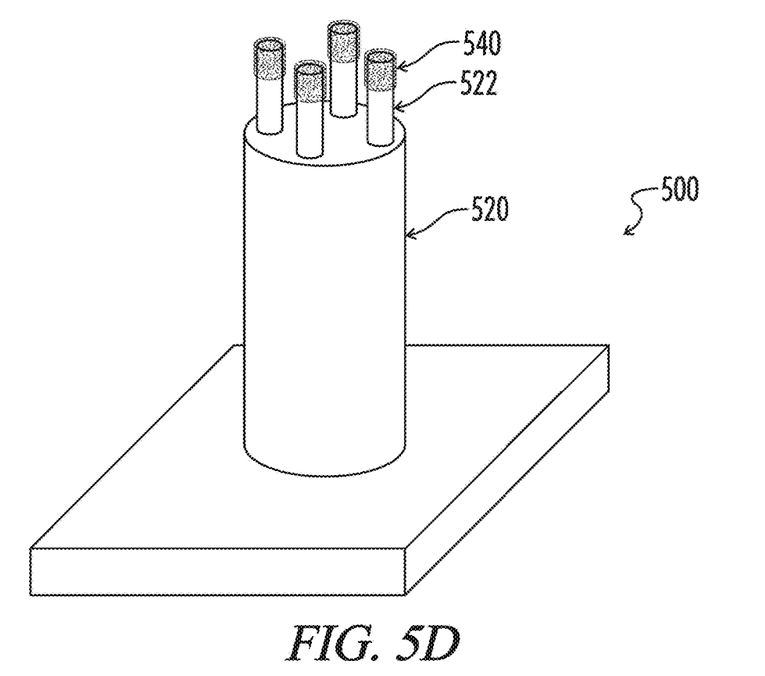
FIG. 5D is a further expanded perspective view of the hierarchical superhydrophobic surface.

An embodiment of a hierarchical superhydrophobic surface comprising a matrix of electrowritten fibers 400 is depicted in FIG. 4. Electrowritten fibers are disposed on a base layer. A non-wetting droplet of a functional solution, e.g., supersaturated solution of the compound to be deposited or a precursor thereof, can be fed by a syringe, pipette, syringe pump or other delivery device and can be linearly translated across the electrowritten surface in a precipitate writing process. As a result, a pattern of localized precipitate deposits, molecules or colloidal particles can be produced on a fibrous matrix. The delivery device can be in communication with a reservoir of functional solution (not shown) and so can continually replenish the growth solution as deposition is ongoing. At the leading contact edge, the solution can contact the terminal level of surface (e.g. nanofibers) and nucleation can be initiated. As the droplet of solution is drawn over the surface, additional material can be deposited from solution and the precipitates can grow. If the material, structure and growth conditions are such that the deposition is adherent, the deposited materials can remain on the substrate as the droplet continues to traverse the substrate. The deposits can remain on the terminal level. As a result, deposited material can be localized to the terminal level of the surface.

Surface Pretreatments

Pretreatments comprise different processes that functionalize the surface of the geometric features, such as oxygen plasma, gold coating, and self-assembled monolayer attachment. For example, non-water based liquids or liquids having low surface tension (e.g., ethanol) can be used as a suitable solvent to introduce thiolated molecules to the terminal level of a surface. Such processes are expected to coat along the entire surface of the texture features; however, the superhydrophobic nature of the structure is expected to prevent complete wetting when later exposed to a growth solution (e.g., a water-based growth solution). For example, a negatively charged superhydrophobic surface created by exposure to thiol can then interact with, for example, positively charged particles to form particles attached onto the superhydrophobic surface.

Examples of surface groups that can provide positive charges include amine groups, which could be achieved using alkanethiol self-assembled monolayer species such as ammonium salts, including but not limited to $HS(CH_2)_{11}NH_3^+Cl^-$, $HS(CH_2)_{11}NMe_3^+Br^-$, or $HS(CH_2)_{11}C(NH_2)^2{}^+Cl^-$, or from colloidal particles having amine groups, such as polystyrene particles synthesized with amidine surface groups.

Examples of surface groups that can provide negative charges include carboxylic acid (—COOH), phosphate (—$PO_3H_2$), or sulfate (—$SO_3$) which could be achieved using alkanethiol self-assembled monolayers such as HS(C)nCOOH, HS(C)nSH, or HS(C)nP, or having a silica surface having a multitude of silanol (Si—OH) groups which can become negatively-charged over a range of pH.

Hydrogen bonding can be involved with strongly interacting charged groups such as amine (—$NH2$) and —OH groups.

Covalent bonding can be achieved through the reaction between carboxylic acid (—COOH) with an amine group (—$NH2$). Such types of covalent bonding reactions are involved in protein binding interactions.

Electrostatic attraction could also be achieved by applying a potential to a conductive superhydrophobic surface, for the electrophoretic attachment of oppositely-charged particles. For example, the attachment of negatively charged particles (such as SiO2 particles in basic conditions, or polystyrene particles with sulfate groups) onto a pillar structure with a positive charge from an applied potential.

As noted above, the interaction between the particles and the superhydrophobic surface need not be limited to electrostatic interactions as exemplified above. Other suitable interactions can include any surface chemistries one of ordinary skill in the art would readily recognize.

FIG. 5 depicts several view of an exemplary hierarchical superhydrophobic surface 500 of the present disclosure. FIG. 5A is a perspective view depicting the surface 500. Substrate 530 forms a base level upon which first geometric features 520 are disposed. Additional geometric features of the surface are not depicted in FIGS. 5A and B for simplicity. As seen in FIG % B, which is a top view of the surface 500, geometric features 520 may be ordered as depicted or disordered. The substrate 530 can form a medical device or implant, such as an implantable sheet, or may provide a surface for any other medical device, such as a stent, retractor, prosthetic, and the like. FIG. 5C is a slightly expanded perspective view of the surface 500, depicting a second set of geometric features 522 disposed on top of features 520 to produce the hierarchical surface. Features 522 may be arranged in an ordered fashion as shown or in a disordered fashion. FIG. 5D depicts a further expanded perspective view depicting terminal level 540 disposed on the tips of second features 522. Terminal level 540 comprises a material having a different hydrophilicity from the substrate material which forms the base layer 530 and features 520 and 522. For example, terminal level 540 may be more hydrophilic than the substrate material or less hydrophilic than the substrate material. Although features 520 and 522 are depicted as pillars, the present surfaces are not so limited and it will be readily understood that the geometric features may comprise pillars, sinusoids, triangular prisms, squares, rectangles, ovals, flutes or combinations thereof.

Figure 6A:
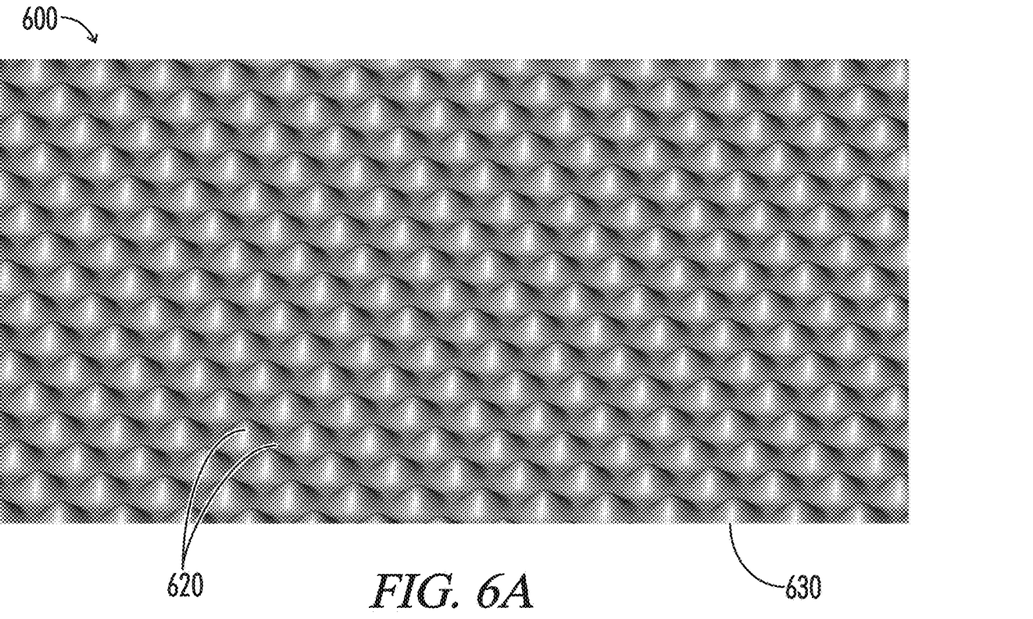
FIGS. 6A and 6B depict an embodiment of a hierarchical superhydrophobic surface according to the present disclosure in which the first geometrical surface is a sinusoidal pattern.
Figure 6B:
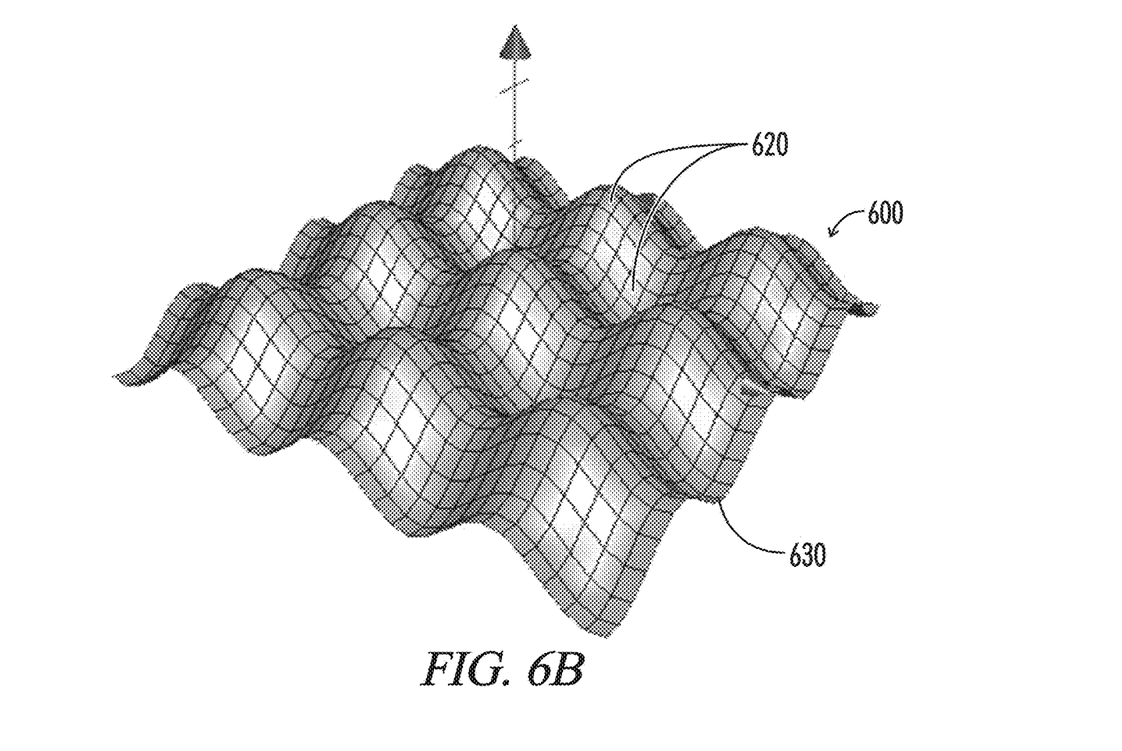

FIG. 6 depicts another embodiment in which the surface 600 comprises a sinusoidal substrate layer 630. FIG. 6A shows a perspective view of an exemplary sinusoidal pattern having sinusoidal peaks 620 disposed thereon. The further geometric features and terminal layer are not shown in FIGS. 6A and 6B for simplicity.

Figure 7A:
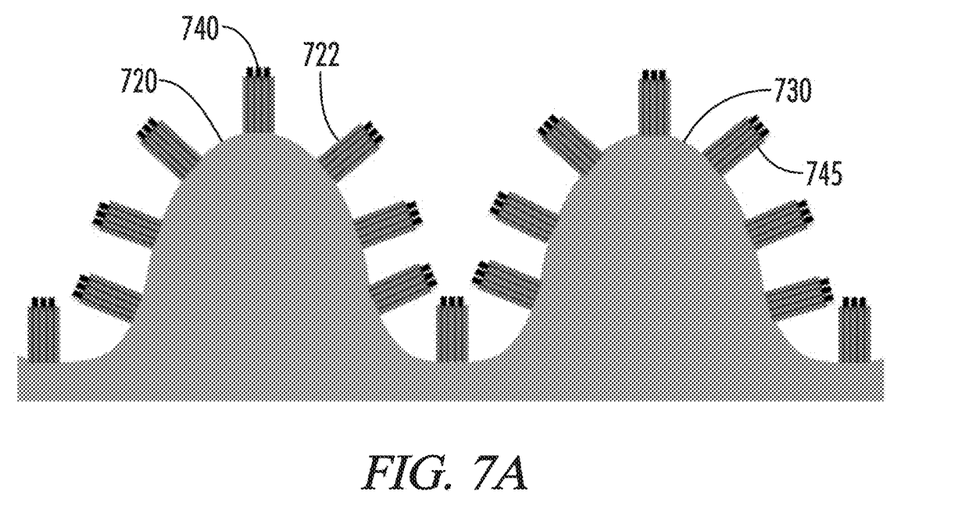
FIGS. 7A and 7B depict an expanded side view of two embodiments of a hierarchical superhydrophobic surface in which the first geometrical structure is a sinusoidal pattern.
Figure 7B:
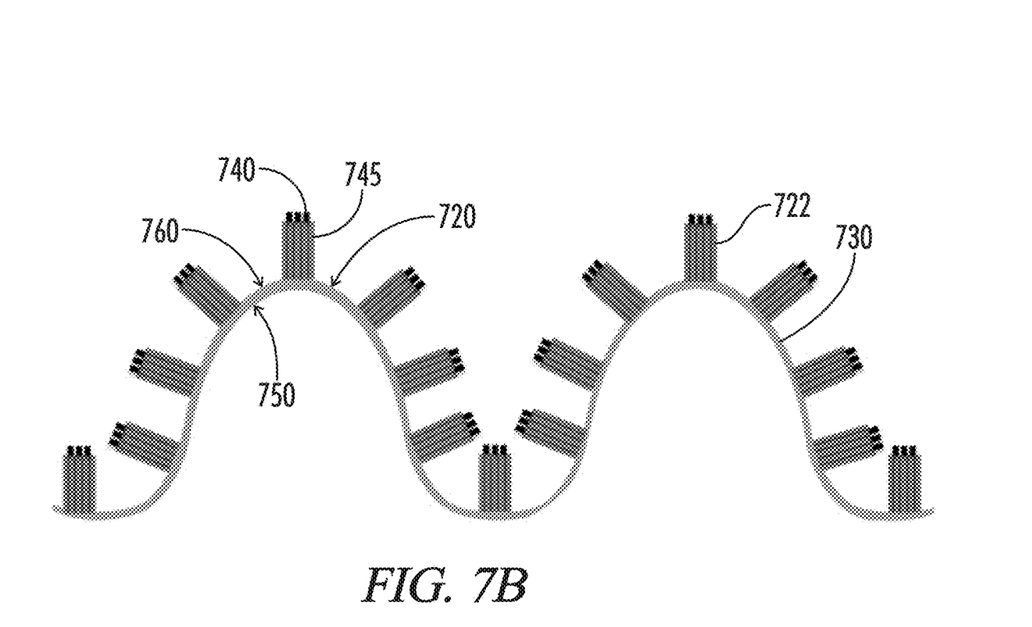

FIGS. 7A and 7B depict a side view of a sinusoidal surface comprising substrate 730 having peaks 720. Further geometrical features 722 are disposed thereon, and terminal level 740 is disposed on features 722. Terminal level 740 comprises a material having a hydrophilicity different from the substrate material 730 that forms the substrate and features 720 and 722. Features 722 may, in some embodiments further include flutes or ridges 745. In FIG. 7A, the substrate 730 comprises a smooth bottom surface. In FIG. 7B, substrate 730 is a thin film having a top surface 760 and a complimentary shaped bottom surface 750.

EXAMPLE 1

Nucleation of CaCO3 Particles

A surface of pillars on top of pillars was prepared from non-crosslinked polyurethane by solvent casting on a silicon inverse mold of the desired surface structure. The terminal level, due to its higher pillar density will be more hydrophilic than the larger pillar structure. Accordingly the terminal level will preferentially attract ionic solutions. A 50 mM aqueous solutions of ionic CaCl2 was prepared from CaCl2 (Sigma-Aldrich) in distilled water. The CaCl2 solution is lightly and uniformly coated on a flat hydrophilic surface. The surface is placed terminal level down on the surface, whereby the CaCl2 selectively adheres to the terminal level. The CaCl2, residing on the surface was then placed in a chamber and exposed to a flow of carbon dioxide gas from a nitrogen gas flow over ammonium carbonate powder ((NH4)2CO3, Sigma-Aldrich). After about 30 minutes, the droplets were removed from the substrate by evaporation, and the substrates removed from the chamber. The result is a monodisperse array of CaCO3 particles filling the terminal level of the surface.

EXAMPLE 2

Nucleation of Fe3O4 Particles

A surface of pillars on top of pillars was prepared from non-crosslinked polyurethane by solvent casting on a silicone inverse mold of the desired hierarchical superhydrophobic surface. The terminal level, due to its higher pillar density will be more hydrophilic than the larger pillar structure. Accordingly the terminal level will preferentially attract ionic solutions. An aqueous solution of ionic FeCl2 was prepared from FeCl2 (Sigma-Aldrich) in distilled water. The FeCl2 solution is lightly and uniformly coated on a flat hydrophilic surface. The hierarchical surface is placed terminal level down on the surface, whereby the FeCl2 selectively adheres to the terminal level. The prepared hierarchical surface was exposed to an atmosphere of NH3 using ammonia solution in a closed chamber. The ammonia caused the precipitation of Fe3O4. After about 10 minutes, the droplet was removed to leave behind the deposit of Fe3O4 nanoparticles encasing the terminal level.

EXAMPLE

Terminal Level Substitution of Polyurethane

An hierarchical surface formed from a mold comprised of a first level two-dimensional sinusoid, a second level pillar array, and a terminal level pillar array, and the terminal level pillar array includes flutes evenly spaced circumferentially on the external walls of the terminal level pillars. The surface comprises polylactic acid. The hierarchical superhydrophobic surface was placed in a tray with the first level down and anchored to the bottom of the tray. Then the tray was filled to a level coincident with the tops of the level two pillars and allowed to cure. A solution of polyurethane was prepared by dissolving 10% w/w polyurethane in acetone. The solution was poured over the silicone layer, and a flat sheet of silicone placed on top. The acetone diffuses into the silicone and precipitates the polyurethane on the terminal level selectively. The top layer of silicone is removed. The interstitial layer of silicone is removed, leaving a polylactic acid hierarchical superhydrophobic surface having a terminal level functionalized with polyurethane.

Shear Test of Hierarchicalsuperhydrophobic Surfaces

Hierarchical superhydrophobic surfaces comprising of pillars on top of pillars were prepared and tested for shear properties when placed against beef steak. The test articles were hierarchical surfaces alone and surfaces with the terminal level functionalization. Polyurethane (AP1780), polylactic acid (PLA) and Silicone were the test materials. All results are given in lbs/cm2 units. Each surface was tested five times.

TABLE 1

Shear test

| Test Article | Shear Force lbs/cm$^2$ |
| --- | --- |
| Hierarchical surface without terminal level modification | |
| AP1780 | 0.046 +/− 0.007 |
| PLA | 0.059 +/− 0.005 |
| Hierarchical surface with terminal level modification | |
| AP1780 with PLA terminal level | 0.031 +/− 0.004 |
| PLA with AP1780 f terminal level | 0.068 +/− 0.006 |
| PLA with silicone terminal level | 0.043 +/− 0.004 |

Applications

A wide range of materials can be locally deposited by exposing the terminal level of geometric features to a liquid layer. For example, a suitable liquid can include a range of organic and inorganic compounds that can be deposited from solution. The solution can be aqueous, anhydrous, or lipophilic. The terminal level structures can serve as a deposition and/or a growth site. For example, the terminal level structures can serve as nucleation sites for deposition, as a heterogeneous catalyst for the nucleation and precipitation of the material, or as an adsorption site for the adsorption of molecules on a surface. In other embodiments, the fluid can contain a colloidal suspension of particles that can be deposited on the wetted surfaces of the terminal level, through covalent or non-covalent attachment.

In still other embodiments, the solution treatment can include a first precursor solution to prepare the terminal level for a second solution of deposition material that reacts to form an adherent solid phase. The reaction can include nucleation that results in deposition on the exposed surfaces of the terminal level. For example, the solution can contain a monomer, which is polymerized in the fluid and which is deposited as a polymer on the exposed terminal surfaces of the geometric feature. Alternatively, the deposition fluid can contain a component which reacts to a precursor deposit on the terminal surface of the geometric features when subjected to a suitable reagent or catalyst.

A variety of useful materials can be grown from solution onto the terminal level of hierarchical superhydrophobic surface, to create new structures with chemical or geometrical functionality. For example, a bioactive or catalytic compound could be grown on the terminal level of the hierarchical superhydrophobic surface, providing an array of catalytic or bioactive dots, e.g., adhesive points. The deposited material can be adherent and, as such, can serve as a substrate for further processes, including cell adhesion, protein adsorption, angiogenesis, bacteriostasis, nitric oxide release, and antioxidation.

The above non-limiting exemplary applications make apparent to one of ordinary skill in the art numerous other applications that can be envisioned with the hierarchical superhydrophobic surface surfaces of the present disclosure.

The description provided herein is not to be limited in scope by the specific embodiments described, which are intended as single illustrations of individual aspects of certain embodiments. The methods, compositions and devices described herein can comprise any feature described herein either alone or in combination with any other feature(s) described herein. Indeed, various modifications, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference in their entirety into the specification to the same extent as if each individual publication, patent or patent application was specifically and individually indicated to be incorporated herein by reference. Citation or discussion of a reference herein shall not be construed as an admission that such is prior art.

Thus, although there have been described particular embodiments of the present disclosure of hierarchical superhydrophobic surfaces it is not intended that such references be construed as limitations upon the scope of this disclosure except as set forth in the following claims.

What is claimed is:

1. A superhydrophobic surface comprising a substrate having superhydrophobicity wherein the superhydrophobicity is generated from a microstructure pattern disposed on the substrate, the microstructure pattern including an array of first geometrical features, the array of first geometrical features having a pitch between adjacent features from 10 to 1000 microns, and a terminal level disposed on the array of first geometrical features, wherein the terminal level is a chemical coating, and wherein the microstructure pattern is configured to generate a Wenzel-Cassie state for adhering the substrate to a target surface.

2. The superhydrophobic surface of claim 1, wherein the first geometrical features have a top portion and a side portion, the terminal level being disposed on the top portion.

3. The superhydrophobic surface of claim 1, wherein the first geometrical features are selected from the group consisting of pillars, sinusoids, triangular prisms, flutes, ridges, squares, rectangles, ovals, and combinations thereof.

4. The superhydrophobic surface of claim 3, wherein the first geometrical features comprise a first material.

5. The superhydrophobic surface of claim 4, wherein the terminal level comprises a second material, the second material being different from the first material.

6. The superhydrophobic surface of claim 5, wherein the first material comprises a hydrophobic composition and the second material comprises a hydrophilic composition.

7. The superhydrophobic surface of claim 5, wherein the first material comprises a hydrophilic composition and the second material comprises a hydrophobic composition.

8. The superhydrophobic surface of claim 4, wherein the first material is selected from the group consisting of polylactic acid, polyurethane, polypropylene, silicone or a combination thereof.

9. The superhydrophobic surface of claim 5, wherein the second material is selected from the group consisting of poly(styrene-co-2,3,4,5,6-pentafluorostyrene-SH), poly(methyl methacrylate-co-pentafluorooctyl methacrylate-SH), carboxylic acid-terminated thiols, sulfonated thiol molecules, hydroxyl-terminated thiols, and PEG-terminated thiols.

10. The superhydrophobic surface of claim 1, wherein the first geometrical features comprise a width or diameter ranging from about 1 micron to about 100 microns.

11. A superhydrophobic surface comprising a substrate having superhydrophobicity wherein the superhydrophobicity is generated from a microstructure pattern disposed on the substrate, the microstructure pattern including an array of first geometrical features disposed on the substrate, wherein the array of first geometrical features is a two-dimensional sinusoid having a pitch between adjacent features from 10 to 1000 microns, and a terminal level disposed on the first geometrical features, and a terminal level disposed on the array of first geometrical features, wherein the terminal level is a chemical coating, and wherein the microstructure pattern is configured to generate a Wenzel-Cassie state for adhering the substrate to a target surface.

12. The superhydrophobic surface of claim 11, wherein the array of first geometrical features is ordered.

13. The superhydrophobic surface of claim 11, wherein the array of first geometrical features is disordered.

14. The superhydrophobic surface of claim 11, wherein the first geometrical features comprise a width ranging from about 1 micron to about 100 microns.

15. The superhydrophobic surface of claim 11, wherein the surface including the array of first geometrical features has a surface area of at least 100 times the surface area of a surface having the same dimensions without the microstructure pattern.

16. The superhydrophobic surface of claim 11, wherein the terminal level is bonded or adherent to the array of first geometrical features via van der Waals interaction, covalent interaction, ionic interaction, hydrogen bonding, or combinations thereof.

17. The superhydrophobic surface of claim 11, wherein the first geometrical features comprise a first material, the terminal level comprises a second material, the second material being different from the first material.

18. The superhydrophobic surface of claim 17, wherein the first material comprises a hydrophobic composition and the second material comprises a hydrophilic composition.

19. The superhydrophobic surface of claim 17, wherein the first material comprises a hydrophilic composition and the second material comprises a hydrophobic composition.

20. The superhydrophobic surface of claim 17, wherein the first material is selected from the group consisting of polylactic acid, polyurethane, polypropylene, silicone or a combination thereof, and the second material is selected from the group consisting of poly(styrene-co-2,3,4,5,6-pentafluorostyrene-SH), poly(methyl methacrylate-co-pentafluorooctyl methacrylate-SH), carboxylic acid-terminated thiols, sulfonated thiol molecules, hydroxyl-terminated thiols, and PEG-terminated thiols.

\* \* \* \* \*